US006310937B1

(12) United States Patent
Van Den Hoogenhof

(10) Patent No.: US 6,310,937 B1
(45) Date of Patent: Oct. 30, 2001

(54) X-RAY DIFFRACTION APPARATUS WITH AN X-RAY OPTICAL REFERENCE CHANNEL

(75) Inventor: Waltherus W. Van Den Hoogenhof, Almelo (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/426,522

(22) Filed: Oct. 26, 1999

(30) Foreign Application Priority Data

Oct. 29, 1998 (EP) .................................................. 98203658

(51) Int. Cl.$^7$ .................................................. G01N 23/20
(52) U.S. Cl. .................................................. 378/71
(58) Field of Search .......................................... 378/71–78

(56) References Cited

U.S. PATENT DOCUMENTS 5,155,751 * 10/1992 Chohata et al. ...................... 378/71

FOREIGN PATENT DOCUMENTS

WO9615442    5/1996  (WO) .

* cited by examiner

Primary Examiner—Craig E. Church

(57) ABSTRACT

X-ray diffraction measurements are often carried out in a given atmosphere which may vary in respect of a variety of parameters, such as pressure, temperature, etc. Notably soft X-rays are very sensitive to atmospheric absorption. Therefore, the measured intensity is dependent not only on the material variables to be measured for the sample to be examined (10), but also on the varying absorption which thus constitutes a disturbing influencing of the X-rays in the X-ray optical path (16, 46, 50, 10, 52) from the X-ray source (7) to the detector (30). According to the invention a second X-ray optical path (54, 56, 58, 60) is established; this second path deviates from the first X-ray optical path and serves to carry out reference measurements, during or between the actual measurements, in order to determine the absorption of the atmosphere and to determine a correction factor for the X-ray intensity measured during the actual measurements.

3 Claims, 3 Drawing Sheets

X-RAY DIFFRACTION APPARATUS WITH AN X-RAY OPTICAL REFERENCE CHANNEL

The invention relates to an X-ray diffraction apparatus which includes a sample location for receiving a sample to be examined, an X-ray source for generating X-rays in the sample, a detector for detecting the X-rays emanating from the sample, and correction means for making a correction for a disturbing influencing of the X-rays in the X-ray optical path from the X-ray source to the detector.

An apparatus of this kind is known from the published international patent application WO 96/15442.

An analysis technique which is known as X-ray diffraction is available for X-ray analysis of materials. A sample to be examined is then generally irradiated by means of a monochromatic X-ray beam which is deflected (diffracted) only at given angles (whose value 2θ is measured relative to the forward beam) because of the regularity of the crystal structure of the constituents of the sample. The diffraction angles provide information as regards the crystal structure of the constituents of the sample. The diffraction angles are measured by traversing a (art of) a circle around the sample by means of an X-ray detector while measuring the intensity of the X-rays diffracted by the sample. In a practical arrangement the diffraction angles are generally determined in two ways. According to a first measuring method, the sample to be examined is stationary and the X-ray source and the detector both rotate around the sample at the same speed; this method of measuring is known as a θ—θ scan. According to a second method of measuring, the X-ray source is stationary and the sample to be examined rotates at a given speed while the detector rotates around the sample at twice the speed; this measuring method is known as a θ–2θ scan.

This analysis technique, therefore, requires an X-ray source for generating X-rays in the sample and a detector for detecting the X-rays diffracted by the sample. The X-rays travel along an X-ray optical path which extends from the X-ray source to the detector via the sample. Other X-ray optical elements, such as paralleling collimators for paralleling the beam, beam-limiting diaphragms for limiting background radiation, and monochromator crystals for monochromatizing the X-ray beam, may also be present in said X-ray optical path.

For X-ray diffraction it is important to determine the intensity of the X-rays detected by the detector. It is then desirable to determine the content of a given chemical phase (for example, a compound) in the sample. A problem is then encountered in that these measurements often taken place in a given atmosphere which may vary in respect of a variety of parameters, such as pressure, temperature, humidity, composition, dust content etc. X-rays, notably soft X-rays (i.e. X-rays having a comparatively long wavelength of the order of 1 nm or more) are very sensitive to atmospheric absorption. Therefore, the intensity measured by the detector is dependent not only on the quantities to be measured, but also on the varying absorption which thus constitutes a disturbing influencing of the X-rays in the X-ray optical path from the X-ray source to the detector.

In order to counteract the problems stemming therefrom, the apparatus which is known from the cited international patent application is provided with correction means for correcting said disturbing influencing. The known correction means consist of a number of sensors, each of which picks up a parameter such as pressure, temperature, humidity etc., and a processor which calculates, on the basis of the parameters measured by the sensors and calculation formulas, correction coefficients for correcting the intensity measured by the detector and corrects the intensity on the basis thereof. This known method has the drawback that any disturbing effect must be known in advance and that a separate measuring channel must be available for this purpose, complete with associated formulas for calculating the correction coefficient associated with the relevant disturbing effect. Moreover, it is then assumed that each of the disturbing influences has its own effect on the intensity and that no additional effect occurs due to a combination of disturbing influences. It is difficult and in practice often impossible to correct the effect of the combination of disturbing influences in this known manner.

It is an object of the invention to provide an X-ray analysis apparatus of the kind set forth in which the measured intensity can be corrected for an arbitrary number of disturbing influences, even if these influences are not known in advance, and irrespective of the effect of a combination of the disturbing influences.

To this end, the apparatus according to the invention is characterized in that the correction means include reference means for forming a second X-ray optical path from the X-ray source, which second X-ray optical path extends at least partly separately from the former X-ray optical path and includes a detector for detecting the X-rays emanating from the source.

As a result of the formation of a second X-ray optical path which extends separately from the X-ray optical path intended for the measurements, it is possible to measure the variation of the attenuation of the radiation in the path intended for measurements. The intensity detected via the first path can be continuously or periodically compared with the intensity received via the second path, the intensity in the path intended for measurements being determined in standard circumstances. When the value of the intensity detected in the second path varies by a given factor during the actual measurements, the value of the intensity detected in the first path can be corrected by the same factor.

In an embodiment of the invention, the detector which forms part of the former X-ray optical path and the detector which forms part of the second X-ray optical path are formed by one and the same detector. In cases where it is not desired to monitor the variation of the disturbing influences continuously during the actual measurements but only to observe these influences, for example between the measurements, it suffices to use only one detector which is then used alternately for the actual measurements and for the intensity measurement in the second X-ray optical path in order to determine the variation of the disturbing influences therefrom. The use of only a single detector for the reference measurements as well as the actual measurements, moreover, offers the advantage that any differences between the detectors do not have an effect on the intensity measurements, so that no separate correction is required in this respect.

The second X-ray optical path in a further embodiment of the invention includes an X-ray mirror which is arranged in such a manner that when the sample to be examined is not present in the former X-ray optical path, this mirror reflects the X-rays from the source to the detector. During the actual measurements, the X-ray optical path intended for these measurements is used and the X-ray mirror does not receive radiation because in these circumstances it is situated, for example in the shade of the sample to be examined. During a change of sample, the sample is moved out of its original position, so that the radiation from the X-ray source can reach the mirror. The second X-ray optical path is then formed by the path extending from the source to the detector via the mirror. As long as the mirror receives radiation from the X-ray source, a reference measurement can be carried out so as to determine the disturbing influences. If desired, the period of time elapsing between the measurement of two samples can be slightly prolonged so as to allow for a better reference measurement.

A further embodiment of the apparatus according to the invention includes a parallel plate collimator in which there is provided a bore which forms part of the second X-ray optical path. This step advantageously utilizes the fact that in a parallel plate collimator (also referred to as a Soller slit unit) a major part of the X-rays generated by the X-ray source is intercepted by the plates of the collimator so that an approximately parallel X-ray beam remains. When a bore is provided through the collimator plates, a (small) part of the intercepted X-rays is conducted to the second X-ray optical path where it is used for the reference measurements. This is because for these measurements it is not necessary for the X-rays originating from the X-ray source to be paralleled. This embodiment of the invention is particularly suitable for use in combination with two different detectors, because the reference measurements can then be performed simultaneously with the actual measurements.

The invention will be described in detail hereinafter with reference to the Figures in which corresponding reference numerals denote corresponding elements. Therein:

Figure 1:
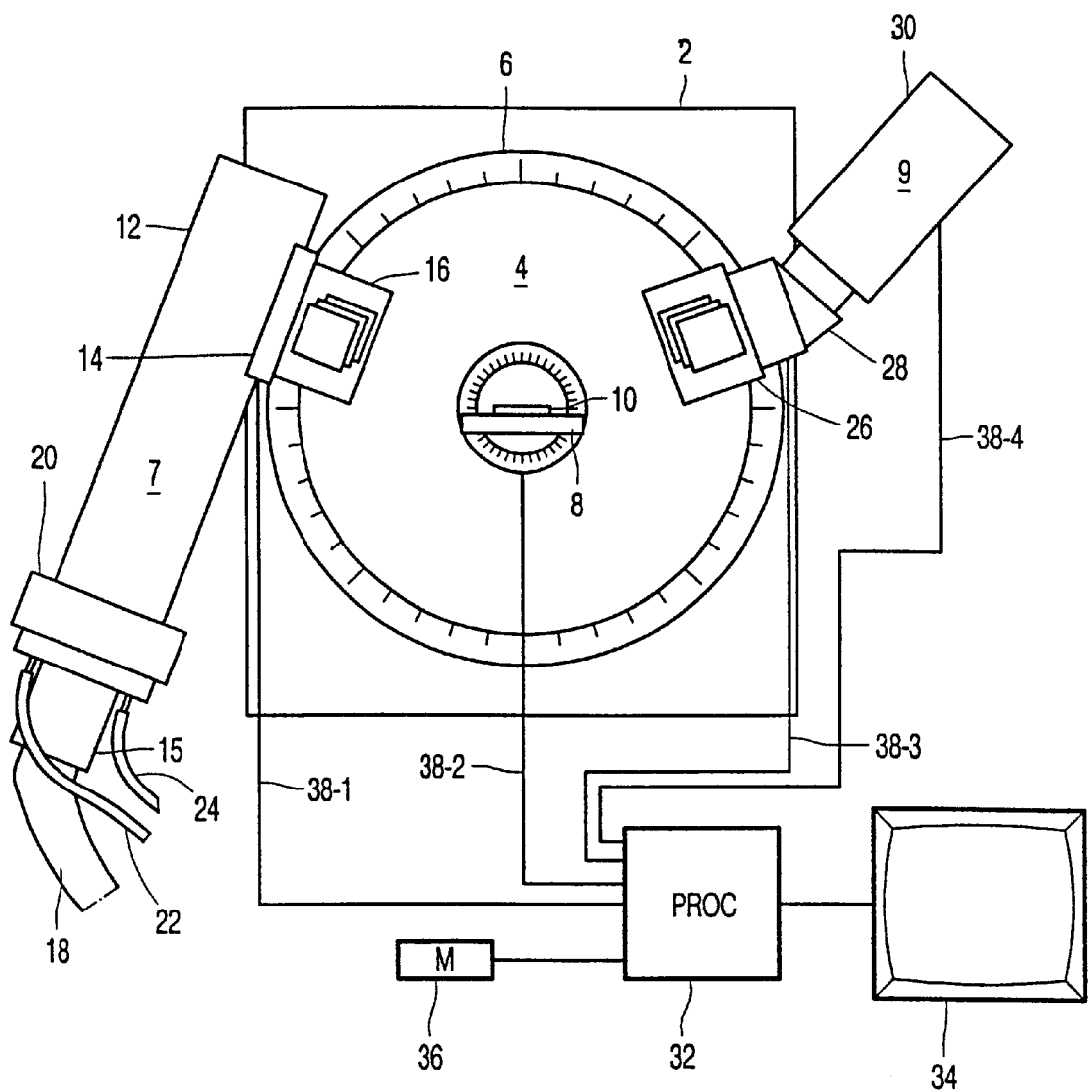
FIG. 1 is a diagrammatic representation of an X-ray analysis apparatus in which the invention can be used.

FIG. 1 is a diagrammatic representation of a known X-ray analysis apparatus, in this case being an X-ray diffraction apparatus. Therein, a goniometer 4 is mounted on a frame 2. The goniometer 4 includes a scale graduation 6 for measuring the angular rotation of the X-ray source 7 mounted thereon and of the detector device 9 which is also mounted thereon. The goniometer is also provided with a sample carrier 8 on which a sample 10 is arranged. In those cases where measurement of the angular rotation of the sample is important, a scale graduation is provided on the sample carrier. The X-ray source 7 includes a holder 12 for an X-ray tube (not shown in this Figure) which is mounted in the holder by way of a fixing ring 20. The X-ray tube is provided with a high-voltage connector 15 via which the high voltage and the filament current for the X-ray tube can be supplied via the high-voltage cable 18. Inlet and outlet ducts 22 and 24 for the cooling water of the X-ray tube are also provided at the same side of the X-ray tube. The tube holder 12 also includes an exit opening for X-rays 14 and a unit 16 for paralleling the X-ray beam (a Soller slit unit). The detector device 9 consists of a holder 26 for a Soller slit unit, a holder 28 for a monochromator crystal, and a detector 30. If the X-ray source and the detector are both rotatable about the sample, as shown in the Figure, it is not necessary for the sample to be arranged so as to be rotatable. However, it is alternatively possible to arrange the X-ray source so as to be stationary, as may be necessary in the case of large and heavy X-ray sources. In that case the sample carrier and the detector should both be rotatable.

The X-ray diffraction apparatus as shown in FIG. 1 also includes a processing device for processing the various data measured. The processing device consists of a central processor unit 32 with a memory unit 36 and a monitor 34 for the presentation of the various data and for the display of the measured and calculated results. The X-ray source 7, mounted on the goniometer 4, the detector device 9 and the sample carrier 8 are all provided with a unit (not shown) for determining the angular position of the relevant element relative to the scale graduation of the goniometer. A signal representing this angular position is applied to the central processor unit 32 via connection leads 38-1, 38-2 and 38-3. Furthermore, the intensity of the X-rays detected by the detector 9 is applied to the central processor unit 32 via a connection lead 38-4.

Figure 2:
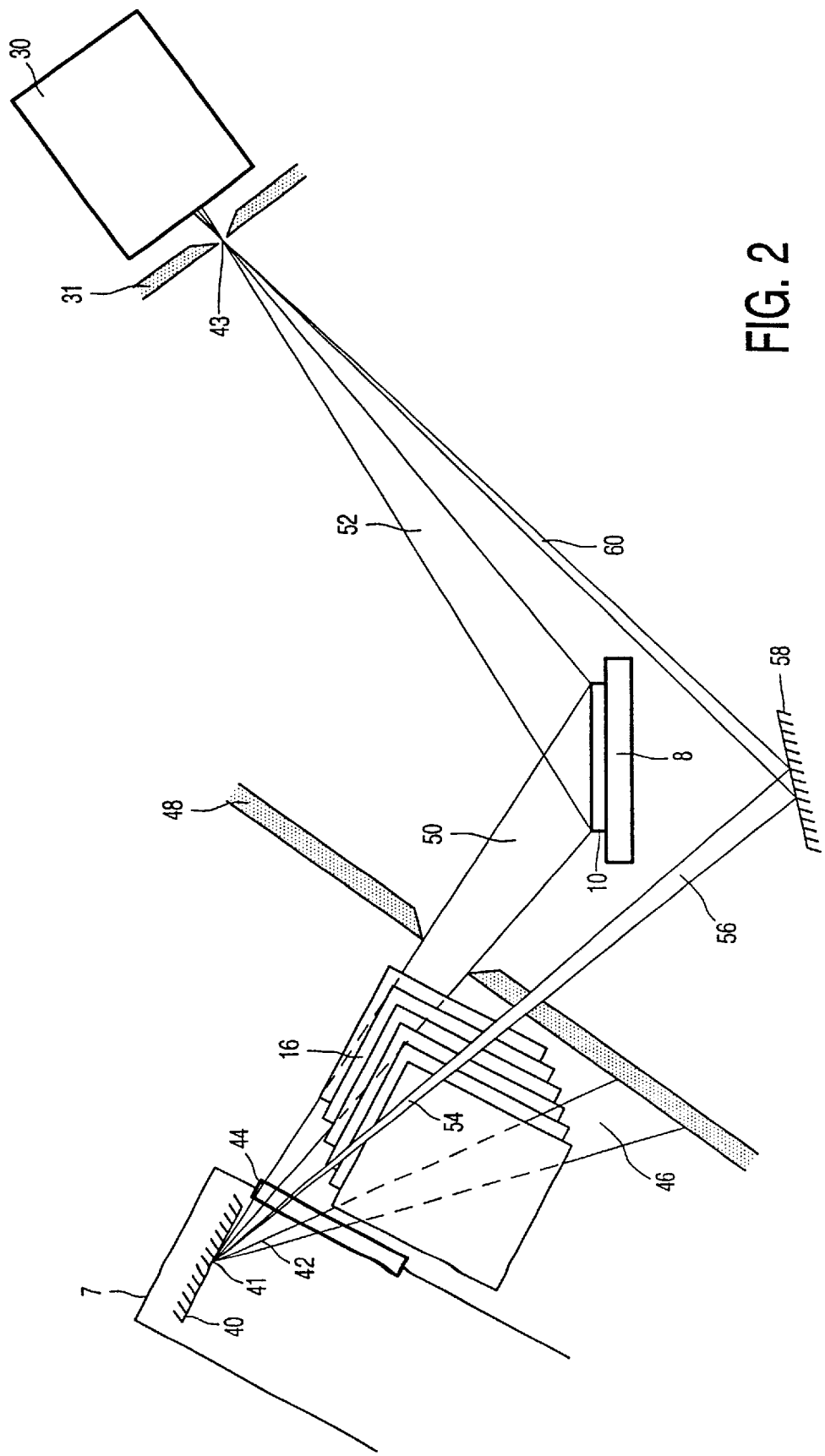
FIG. 2 shows a first embodiment of the invention.

FIG. 2 shows a first embodiment of the invention. This Figure shows only the part of the X-ray analysis apparatus which are of relevance to the invention. The embodiment of FIG. 2 concerns a so-called Bragg-Brentano arrangement, i.e. the X-rays emanating from one point are apparently focused in one point again after reflection on the sample if the surface of the sample is tangent to a circle through the exit point and the focal point.

The sample 10 to be examined is arranged on the sample carrier 8 in FIG. 2. The sample 10 is irradiated by means of X-rays emanating from the X-ray source 7. The X-rays are generated in the X-ray source in a conventional manner by irradiating an anode 40 by means of high-energy electrons. Thus, in the anode X-rays 42 are generated which emanate via an X-ray window 44. In the arrangement shown in FIG. 2 said exit point is not formed by a single point but by a focal line 41 on the anode which extends perpendicularly to the plane of drawing. Said focal point is formed by the union point 43 at the area of the entrance of the detector 30. Consequently, this arrangement has a focusing effect only in the plane of drawing.

Directly behind the X-ray window 44 there is arranged a Soller slit unit 16 for paralleling the X-ray beam 42 emanating from the X-ray source 7. The beam is thus paralleled in planes which extend perpendicularly to the plane of drawing and contain the focal line 41. The X-ray beam 46 thus paralleled subsequently traverses a beam-limiting diaphragm 48 for intercepting the radiation which does not participate in irradiating the sample 10, so that this radiation cannot generate secondary irradiation which disturbs the measurements. After having passed the diaphragm 48, the paralleled and collimated beam 50 is incident on the sample 10 which emits a diffracted beam 52 in the direction of the detector 30 in response to the incident radiation; this beam enters the detector via the exit slit 31 which accurately defines the angular position of the detector entrance. An X-ray optical path 16, 46, 50, 10, 52 is thus established from the X-ray source 7 to the detector 30.

The Soller slit unit 16 consists of a number of mutually parallel plates which, moreover, extend parallel to the plane of drawing and are made of an X-ray absorbing material. Due to the absorption of the non-desirable directions in the X-ray beam 42, a paralleled beam remains in the direction of the sample 10. In the present example, from the X-ray source a second X-ray optical path is established by utilizing the X-rays which would otherwise be absorbed by the Soller slit unit 16 or would be intercepted by the beam-limiting diaphragm 48. To this end, if necessary, an opening is provided in a number of plates of the Soller slit unit 16, said openings together forming a bore 54 in the Soller slit unit; the bore 54 forms part of the second X-ray optical path which is intended for reference purposes. In the Figure the bore 54 is diagrammatically represented as a through-opening in the Soller slit unit 16; in reality this bore can be formed by openings in a limited number of plates, sufficient to transmit enough X-rays for executing a reference measurement with the desired accuracy. Moreover, in the present embodiment a bore is also provided in the diaphragm 48; this bore also forms part of the second X-ray optical path.

The X-ray beam 56 departing from the X-ray source 7 and passing through the bore 54 is then directed onto an X-ray mirror 58. The X-ray mirror 58 reflects the X-rays incident thereon in the form of an X-ray beam 60 in the direction of the detector 60. Thus, a second X-ray optical path 54, 56, 58, 60 is established from the X-ray source 7 to the detector 30. In this case the detector 30 is thus used for the actual measurements as well as for the reference measurements, so that the X-ray apparatus is not available for the actual measurements during the reference measurements. If this is objectionable, a separate detector may be provided for the reference measurements. As has been described with reference to FIG. 1, the intensities measured by the detector are applied, via the connection lead 38-4, to the central processor unit 32 in order to determine the desired correction factor therefrom.

Figure 3:
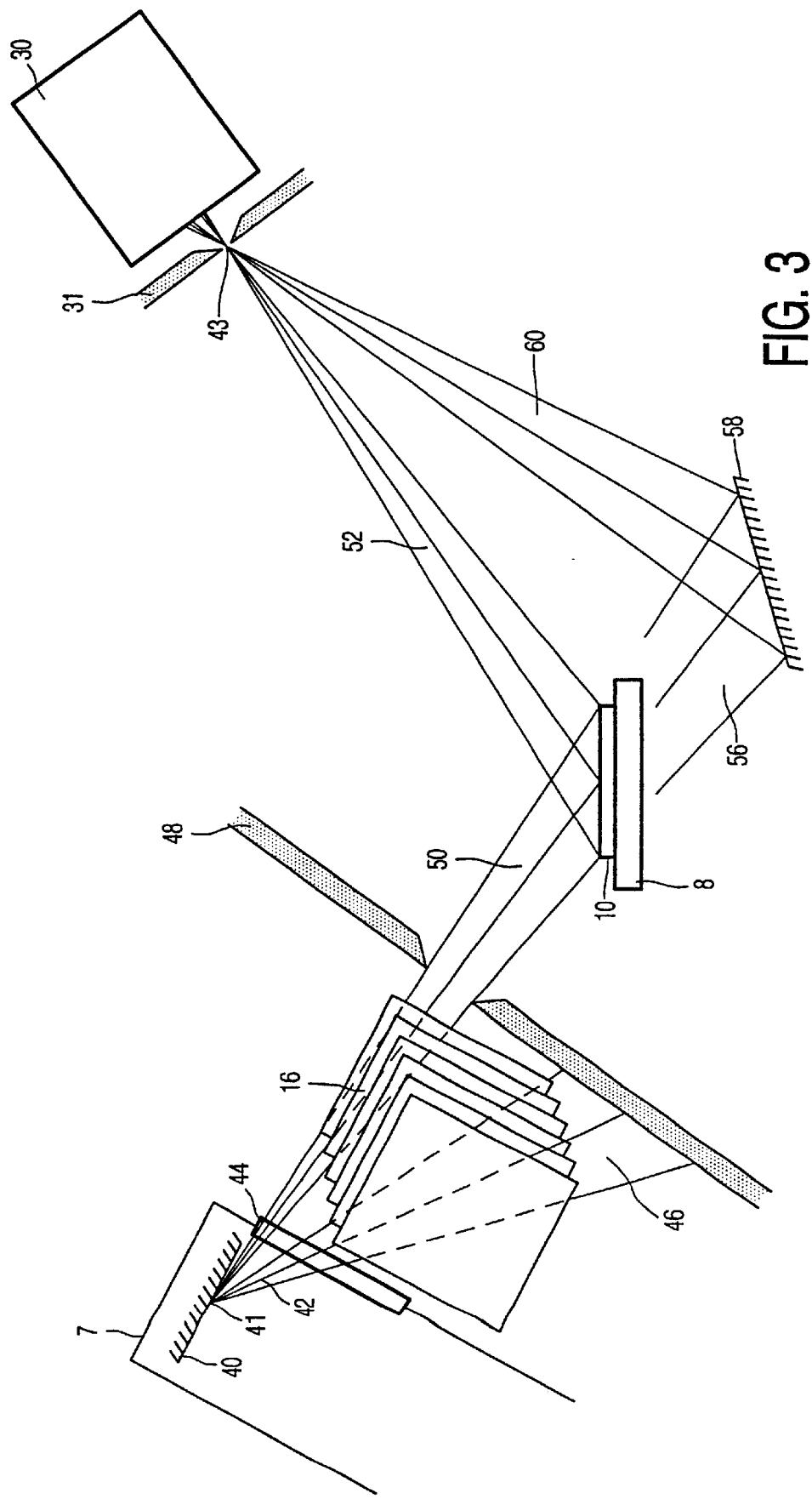
FIG. 3 shows a second embodiment of the invention.

FIG. 3 shows a second embodiment of the invention. A number of elements in FIG. 3 is identical to those in FIG. 2; these elements are denoted by the same reference numerals. As opposed to FIG. 2, in FIG. 3 the second X-ray optical path for reference purposes is realized by arranging the X-ray mirror 58 in such a manner that it is situated in the shade of the sample 10 to be examined when the sample 10 is irradiated by the beam 50. When the sample holder 8 and the sample 10 are not present in the sample location, the X-ray beam 50 is incident on the X-ray mirror 58 so that in that case the beam acts as the reference beam 56. The X-ray mirror 58 reflects this beam to the detector in the form of a beam 60. In the present example the first X-ray optical path between the X-ray source 7 and the detector 30, therefore, is formed by the elements 16, 46, 50, 10 and 52 whereas the second X-ray optical path between the X-ray source 7 and the detector is in this case formed by the elements 16, 46, 50, 56, 58 and 60. In the present embodiment, therefore, the first and the second X-ray optical paths partly coincide, that is to say in the segment formed by the elements 16, 46 and 50.

Like in the embodiment shown in FIG. 2, in the case of FIG. 3 the detector 30 is again used for the actual measurements as well as for the reference measurements, so that X-ray apparatus is not available for the actual measurements during the reference measurements. This method can be used without objection if some time is allowed or required to elapse between the removal of a sample and the positioning of a next sample and if this time suffices to execute a reference measurement.

What is claimed is:

1. An X-ray diffraction apparatus comprising:
   a sample location for receiving a sample;
   an X-ray source for generating X-rays in the sample;
   a detector for detecting the X-rays emanating from the sample; and
   correction means for making a correction for a disturbing influencing of the X-rays in the X-ray optical path from the X-ray source to the detector,
   wherein the correction means include reference means for forming a second X-ray optical path from the X-ray source, which second X-ray optical path extends at least partly separate from the former X-ray optical path and includes a detector for detecting the X-rays emanating from the source and,
   wherein the detector which forms part of the former X-ray optical path and the detector which forms part of the second X-ray optical path are formed by one and the same detector.

2. An apparatus as claimed in claim 1, which includes a parallel plate collimator in which there is provided a bore which forms part of the second X-ray optical path.

3. An apparatus as claimed in claim 2, in which the second X-ray optical path includes an X-ray mirror (58) which is arranged in such a manner that when the sample to be examined is not present in the former X-ray optical path, this mirror (58) reflects the X-rays from the source (7) to the detector (30).

* * * * *